US006972284B2

(12) United States Patent
Fan et al.

(10) Patent No.: US 6,972,284 B2
(45) Date of Patent: Dec. 6, 2005

(54) CHITOSAN AND METHOD OF PREPARING CHITOSAN

(75) Inventors: Weiyu Fan, Minnetonka, MN (US); John A. Bohlmann, Ottumwa, IA (US); James R. Trinkle, Bussey, IA (US); James Donald Steinke, Oskaloosa, IA (US); Ki-Oh Hwang, Oskaloosa, IA (US); Joseph P. Henning, Eddyville, IA (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 09/739,406

(22) Filed: Dec. 18, 2000

(65) Prior Publication Data

US 2002/0025945 A1 Feb. 28, 2002

Related U.S. Application Data

(60) Provisional application No. 60/189,560, filed on Mar. 15, 2000.

(51) Int. Cl.[7] .................. A01N 43/04; A61K 31/722
(52) U.S. Cl. .............. 514/55; 424/195.15; 424/195.16; 424/405; 435/254.1
(58) Field of Search ...................... 435/254.1; 210/640; 514/55; 424/195.15, 195.16

(56) References Cited

U.S. PATENT DOCUMENTS

| 2,040,879 | A |   | 5/1936  | Rigby              |         |
|-----------|---|---|---------|--------------------|---------|
| 4,056,432 | A |   | 11/1977 | Slagel et al.      |         |
| 4,282,351 | A |   | 8/1981  | Muzzarelli         |         |
| 4,806,474 | A | * | 2/1989  | Hershberger ......... | 435/101 |
| 4,886,541 | A |   | 12/1989 | Hadwiger           |         |
| 4,948,881 | A |   | 8/1990  | Naggi et al.       |         |
| 4,970,150 | A |   | 11/1990 | Yaku et al.        |         |
| 4,983,304 | A | * | 1/1991  | Tsugita et al. ........ | 210/640 |
| 5,219,749 | A |   | 6/1993  | Bouriotis et al.   |         |
| 5,232,842 | A |   | 8/1993  | Park et al.        |         |
| 5,730,876 | A |   | 3/1998  | You et al.         |         |
| 5,905,035 | A | * | 5/1999  | Okada et al. ......... | 435/254.1 |
| 5,985,644 | A |   | 11/1999 | Roseman et al.     |         |
| 6,333,399 | B1| * | 12/2001 | Teslenko et al. ...... | 536/20  |

FOREIGN PATENT DOCUMENTS

| EP | 0 885 954 A1 | 12/1998 |
|----|--------------|---------|
| GB | 458839       | 12/1936 |
| JP | 55 012109 A  | 1/1980  |
| JP | 62070401 A2  | 3/1987  |
| JP | 63097633 A2  | 4/1988  |
| JP | 63225602 A   | 9/1988  |
| JP | 2149335 A2   | 6/1990  |
| JP | 2180903 A2   | 7/1990  |
| JP | 2200196 A2   | 8/1990  |
| JP | 2229832 A2   | 9/1990  |
| JP | 2258740 A2   | 10/1990 |
| JP | 5068580 A2   | 10/1993 |
| JP | 7330808 A2   | 12/1995 |
| JP | 08 041106 A  | 6/1996  |
| JP | 10297913 A2  | 11/1998 |
| WO | WO 98/42755  | 10/1998 |
| WO | WO 00/04182  | 1/2000  |

OTHER PUBLICATIONS

Stainer, R. et al., "The Microbial World", *Prentice–Hall, Inc.*, pp. 332–336 (1970).
Arcidiacono, S. et al., "Molecular Weight Distribution of Chitosan isolated from *Mucor rouxii* under Different Culture and Processing Conditions", *Biotechnology And Bioengineering*, vol. 39, pp. 281–286 (1992).
Mima, S. et al., "Highly Deacetylated Chitosan and Its Properties", *Journal of Applied Polymer Sciences*, vol. 28, pp. 1909–1917 (1985).
Alonso, I. et al., "Determination of the Degree of Acetylation of Chitin and Chitosan by Thermal Analysis", *Journal of Thermal Analysis*, vol. 28, pp. 189–193 (1983).
Bartnicki–Garcia, S., "Cell Wall Chemistry, Morphogenesis, and Taxonomy of Fungi", *Chemistry of Fungal Cell Wall* pp. 87–108 (1968).
Benjakul, S. et al., "Improvement of Deacetylation of Chitin from Black Tiger Shrimp (*Penaeus monodon*) Carapace and Shell", *ASEAN Food Journal*, vol. 9, No. 4, pp. 136–140 (1994).
Beri, R. et al., "Characterization of Chitosans via Coupled Size–Exclusion Chromatography and Mutiple–Angle Laser Light–Scattering Technique", *Carbohydrate Research*, vol. 238, pp. 11–26 (1993).
Carlson, T. et al., "Chitin/Chitosan Extraction from *A Niger* Mycelium", *Cargill Central Research*, 16 pages (Aug. 1997).
"Chitin/Chitosan Specifications", *Biopolymer Engineering, Inc.*, http://www.biopolymer.com/spec.htm, 1 page (Date Printed Mar. 4, 1999).
Davies, D. et al., "Determination of the Degree of Acetylation of Chitin and Chitosan", *Methods in Enzymology*, vol. 161, Part B, pp. 442–446 (1988).
Domszy, J. et al., "Evaluation of Infrared Spectroscopic Techniques for Analysing Chitosan", *Makromal. Chem.*, vol. 186, pp. 1671–1677 (1985).
Farkas, V., "Fungal Cell Walls: Their Structure, Biosynthesis and Biotechnological Aspects", *Acta Biotechnol.*, vol. 10, No. 3, pp. 225–238 (1990).
Fleet, G. et al., "17 Fungal Glucans –Structure and Metabolism", *Encyclopedia of Plant Physiology*, vol. 13B, New Series, pp. 416–440 (1981).

(Continued)

*Primary Examiner*—Neil S. Levy
(74) *Attorney, Agent, or Firm*—Paula A. DeGrandis

(57) ABSTRACT

A highly deacetylated chitosan obtained from microbial biomass, a method of obtaining chitosan from microbial biomass, and biomass for making chitosan are disclosed. The method includes providing chitin-containing biomass; reacting the chitin-containing biomass in a caustic solution of greater than 25 percent alkali at a reaction temperature greater than 95° C. for a reaction period of at least 10 hours to convert the chitin in the biomass to chitosan; and separating the chitosan from the caustic solution.

20 Claims, No Drawings

OTHER PUBLICATIONS

Gassner, G. et al., "Teichuronic Acid Reducing Terminal N–Acetylglucosamine Residue Linked by Phosodiester to Peptidoglycan of *Micrococcus luteus*", *J. Bacteriol.*, vol. 172, No. 5, pp. 22732279 (May 1990).

Gobin, P. et al., "Structural Chemistry of Fungal, Polysaccharides", pp. 367–417 (1968).

Johnston, I., "The Composition of the Cell Wall of *Asperigillus niger*", *Biochem, J*, vol. 96, pp. 651–658 (1965).

Kurita, K., "Controlled Functionalized of the Polysaccharide Chitin", *Prog. Polym. Sci.*, vol. 26, pp. 1921–1971 (2001).

Kurita, K. et al., "Studies on Chitin, 3, Preparation of Pure Chitin, Poly(N–acetyl–D–glucosamine), from the Water–Soluble Chitin", *Makromal. Chem.*, vol. 178, pp. 2595–2602 (1977).

Kurita, K. et al., "Studies on Chitin, 4, Evidence for Formation of Block and Random Copolymers of N–Acetyle–D–glucosamine and D–Glucosamine by Hetero– and Homogeneous Hydrolyses", *Makromol. Chem.*, vol. 178, pp. 3197–3202 (1977).

Maghami, G. et al., "Evaluation of the Viscometric Constants for Chitosan", *Makromol. Chem.*, vol. 189, pp. 195–200 (1988).

Muzzarelli, R. et al., Chelating, Film–Forming, and Coagulating Ability of the CitosanGlucan Complex from *Aspergillus niger* Industrial Wastes, *Biotechnology and Bioengineering*, vol. XXII, pp. 885–896 (1980).

Nanjo, F. et al., "Enzymatic Method for Determination of the Degree of Deacetylation of Chitosan", *Analytical Biochemistry*, vol. 193, pp. 164–167 (1991).

Niola, F. et al., "A Rapid Method for the Determination of the Degree of N–acetylation of chitin–chitosan samples by acid hydrolysis and HPLC", *Carbohydrate Research*, vol. 238, pp. 1–9 (1993).

No, H. et al., "Preparation and Characterization of Chitin and Chitosan—A Review", *Journal of Aquatic Food Product Technology*, vol. 4, No. 2, pp. 27–52 (1995).

Novikov, V. et al., "Synthesis of D(+)–Glucossamine Hydrochloride", *Russion Journal of Applied Chemistry*, vol. 70, No. 9, pp. 1467–1470 (1997).

Ottoy, M. et al., "Preparation and Analytical Size–exclusion Chromatography of Chitosans", *Carbohydrate Polymers*, vol. 31, pp. 253–261 (1996).

Pelletier, A. et al., "Chitin/Chitosan Transformation by Thermo–Mechano–Chemical Treatment Including Characterization by Enzymatic Depolymerization", *Biotechnology and Bioengineering*, vol. 36, pp. 310–315 (1990).

Rege, P. et al., "Chitosan Processing: Influence of Process Parameters During Acidic and Alkaline Hydrolysis and Effect of the Processing Sequence on the Resultant Chitosan's Properties", *Carbohydrate Research*, vol. 321, Nos. 3–4, pp. 235–245 (Oct. 15, 1999).

Roberts, G. et al., "Determination of the Viscomtric Constants for Chitosan", *Int. J. Biol*, vol. 4, pp. 374–377 (Oct. 1982).

Rokem, J. et al., "Degradation of Fungal Cell Walls Taking into Considerstion the Polysaccharide Composition", *Enzyme Microb. Technol.*, vol. 8, No. 10, pp. 588–592 (Oct. 1986) (Abstract).

Ruiz–Herrera, J., "Chemical Components of the Cell Wall of *Aspergillus* Species", *Archives of Biochemistry and Biophysics*, vol. 122, pp. 118–125 (1967).

Sabnis, S. et al., "Improved Infrared Spectroscopic Method for the Analysis of Degree of N–deacetylation of Chitosan", *Polymer Bulletin*, vol. 39, pp. 67–71 (1997).

Sannan, T. et al., "Studies on Chitin, 2, Effect of Deacetylation on Solubility", *Makromol. Chem.*, vol. 177, pp. 3589–3600 (1976).

Shahidi, F. et al., "Food Applications of Chitin and Chitosans", *Trends in Food Science & Technology*, vol. 10, pp. 37–51 (1999).

Stagg, C. et al., The Characterization of a Chitin–Associated D–Glucan from the Cell Walls of *Aspergillus Niger*, vol. 320, pp. 64–72 (1973).

Tan, S. et al., "The Degree of Deacetylation of Chitosan: Advocating the First DerivativeUV–spectrophotometry Method of Determination", *Talanta*, vol. 45, pp. 713–719 (1998).

Wessels, J. et al., "15 Fungal Cell Walls: A Survey", *Plant Carbohydrates II, Extracellular Carbohydrates*, pp. 352–394 (1981).

Wu, et al., "Determination of Molecular–Weight Distribution of Chitosan by High–performance Liquid Chromatography", *Journal of Chromatography*, vol. 128, pp. 87–99 (1976).

* cited by examiner

US 6,972,284 B2

CHITOSAN AND METHOD OF PREPARING CHITOSAN

REFERENCE TO CO-PENDING APPLICATION

This application is a Continuation-in-Part of provisional application Serial No. 60/189,560, filed Mar. 15, 2000.

FIELD OF THE INVENTION

The present invention is directed to chitosan and methods of deriving chitosan from chitin-containing biomass.

BACKGROUND

Chitin is a natural polysaccharide present in various marine and terrestrial organisms, including crustacea, insects, mollusks, and microorganisms, such as fungi. The structure of chitin is that of an unbranched polymer of 2-acetoamido-2-deoxy-D-glucose (N-acetyl-D-glucosamine), and can be represented by the general repeating structure:

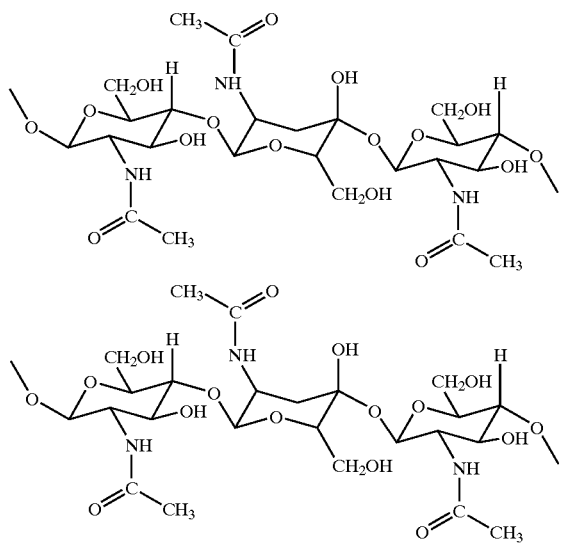

Chitin is typically an amorphous solid that is largely insoluble in water, dilute acids, and alkali. Although chitin has various commercial applications, greater commercial utility is found by converting chitin to the deacetylated product chitosan. Chitosan can be created by N-deacetylation of the chitin polymer, and its structure may be represented by the following general formula, wherein at least some of the acetylamine groups have been converted to amine groups:

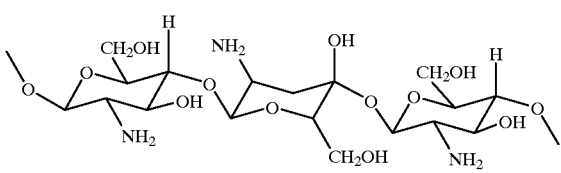

Chitosan is also an amorphous solid that is largely insoluble in water, but is soluble in aqueous organic acids, such as formic and acetic acids. However, the deacetylation reaction is typically not complete, and some of the acetyl groups remain in most chitosan compositions. In the representation above, all of the formerly acetylated amine groups have been converted to amine groups.

Chitosan has many industrial, medical, pharmaceutical, and nutritional uses, including those requiring a biodegradable, non-toxic polymer. For example, chitosan is used as a polyelectrolytic coagulant and a sludge dewatering aid in wastewater treatment. Medical, pharmaceutical, and nutritional uses often require a higher quality chitosan for functional and aesthetic reasons. These uses include applications as anticoagulants, antiviral agents, drug carriers, cosmetic additives, dialysis membranes, orthopedic materials, wound dressings, food stabilizers and thickeners, flavor and nutrient carriers, and dietary fiber.

The quality of chitosan varies with the degree of substitution of the N-acetyl groups, degree of polymerization, manufacturing process, color, clarity, consistency, uniformity, and source. Most chitosan is formed by dissolving calcium carbonate from the shells of aquatic crustacea to liberate chitin, deacetylating the chitin to form chitosan, followed by recovery and drying of the chitosan. One problem with recovery from crustacea is that it is very difficult to obtain uniform, high quality chitosan. The uniformity problems occur in part because the crustacea typically are varying sizes, ages, and species; grow under varied environmental conditions; and are gathered from different locations. The quality issues arise in part due to the fact that sufficiently uniform chitosan cannot be obtained, but also include the fact that chitosan obtained from crustacea often has high ash content and can contain heavy metals that is concentrated in the crustacea from their aquatic environment. A further problem with chitosan derived from harvested crustacea is that it has the potential to include undesired proteins and allergens.

Other methods of producing chitosan involve recovery from microbial biomass, such as the method taught by U.S. Pat. No. 4,806,474. Unfortunately, existing methods of recovering chitosan from microbial biomass need improvement to produce higher quality chitosan that is more suited for pharmaceutical, nutritional and cosmetic applications. For example, a need exists for chitosan having improved consistency and solubility, as well as higher levels of deacetylation than is currently practiced. Present processes do not allow for sufficiently high levels of deacetylation while also providing high quality chitosan from a consistent and controlled raw material source. For example, deacetylation levels of less than 75 percent can be obtained by methods taught in U.S. Pat. No. 4,806,474 to Herschberger, but even higher deacetylation levels are desired. When these higher deacetylation levels are obtained, it is also desirable that other properties of the chitosan be retained or improved. Another method, taught by U.S. Pat. No. 4,282,351, teaches only how to create a chitosan-beta-glucan complex.

Therefore, a need exists for an improved chitosan material that is obtained utilizing an improved method.

SUMMARY OF THE INVENTION

The present invention is directed to chitosan obtained from microbial biomass, a method of obtaining chitosan from microbial biomass, and biomass for making quality chitosan. Chitosan of the present invention typically has at least 85 percent deacetylation levels, frequently 90 percent deacetylation of the acetyl groups in the chitin, and often greater than 95 percent deacetylation. Thus, the compositions typically have an acetylation level of less than 15 percent, frequently less than 10 percent, and often less than 5 percent. This level of deacetylation provides a high quality chitosan with consistent properties that is readily soluble in a slightly acidic solution.

Chitosan recovered in accordance with the present invention can also have improved properties over prior chitosan produced from microbial biomass as well as from shells from aquatic invertebrates, such as plankton. Some chitosan prepared in accordance with the invention can have high solubility and low viscosity compared to that which is known in the art. For example, specific chitosan material prepared in accordance with the invention may have a viscosity of less than 25 centipoise when a 1% solution of the chitosan is dissolved in 1% aqueous acetic acid solution at 25° C.; and may have a viscosity of less than 15 centipoise in some implementations under these conditions.

The method of making the chitosan of the present invention includes providing a consistent chitin-containing biomass; reacting the chitin-containing biomass in a caustic aqueous solution of greater than 25 percent alkali at a reaction temperature greater than 95° C. for a reaction period of at least 10 hours to convert the chitin in the biomass to chitosan; and separating the chitosan from the caustic solution. In one implementation of the invention, the chitin-containing biomass is reacted in a caustic solution of greater than 25 percent alkali at a reaction temperature from 105 to 125° C. for a reaction period of 10 to 16 hours to convert the chitin in the biomass to chitosan. More generally, the chitin-containing biomass is typically reacted in a caustic solution that is from 30 to 40 percent alkali. Suitable reaction temperatures for reacting the biomass are generally less than 125° C., and reaction periods are generally from 10 to 20 hours, and typically from 10 to 16 hours. The method of obtaining chitosan from microbial biomass may also include washing the deacetylated biomass with a caustic solution, recovery of the chitosan, precipitating the chitosan, and drying the precipitated chitosan.

In addition to the primary deacetylation reaction, a pre-treating step may also be used in which the microbial biomass is heated in a less alkaline solution prior to reacting it in a more alkaline solution to deacetylate the chitin. Typically the alkaline concentration is initially below 10 percent for this pre-treatment step and subsequently raised to greater than 25 percent for the primary reaction. In specific pre-treatment implementations, the biomass is first heated in a caustic concentration of about 2 to 5 percent alkali for 0.5 to 4.0 hours at a temperature of 100 to 120° C. This pre-treatment aids in removing excess proteins and various contaminants to provide a higher quality chitosan.

The chitosan is prepared from chitin contained in microbial biomass, and in particular fungal biomass. Suitable microbial biomasses include *Aspergillus niger, Aspergillus terreus, Aspergillus oryzae, Lactarius vellereus, Mucor rouxii, Penicillium chrysogenum, Penicillium notatum, Saccharomyces cerevisiae;* and in particular *Candida guillermondi, Aspergillus niger,* and *Aspergillus terreus.* Preferably, the biomass is recovered from a commercial fermentation reaction, such as the commercial production of organic acids, such as citric acid. As use herein, the term microbial does not include phyto-plankton and crustaceans or mollusks.

The above summary of the present invention is not intended to describe each disclosed embodiment of the present invention. This is the purpose of the detailed description and claims which follow.

DETAILED DESCRIPTION OF THE INVENTION

The present invention is directed to chitosan obtained from microbial biomass, to a method of obtaining chitosan from microbial biomass, and to biomass for making chitosan. The chitosan is typically derived from substantially uniform fungal sources, and has superior properties relative to known products. The method includes providing chitin-containing biomass; reacting the chitin-containing biomass in a caustic solution of greater than 25 percent alkali at a reaction temperature greater than 95° C. for a reaction period of at least 10 hours to convert the chitin to chitosan; and separating the chitosan from the caustic solution.

Specific aspects of the chitosan, biomass, and method of the invention are described below.

Chitosan

Chitosan as produced with the present invention has improved properties over prior chitosan produced from microbial biomass. Some chitosan prepared in accordance with the invention has high solubility and low viscosity compared to that which is known in the art. For example, some chitosan material of the present invention has a viscosity of less than 25 centipoise when dissolved in a 1% solution of the separated chitosan in 1% acetic acid; and may have a viscosity of less than 15 centipoise in some implementations.

Chitosan of the present invention typically has at least 85 percent deacetylation of the acetyl groups in the chitin, frequently at least 90 percent deacetylation, and often greater than 95 percent deacetylation. These levels of deacetylation provides a high quality chitosan that is readily soluble in slightly acidic solution. Notably, these deacetylation levels are obtained without excessive damage to the chitosan molecule. Thus, the molecule can maintain its integrity while improving performance.

In addition, the chitosan of the present invention typically has greater uniformity than that observed in prior chitosan. This uniformity includes, for example, viscosity, color, and deacetylation levels. An additional improvement of the present chitosan is that it has low ash levels, typically less than 0.50 percent. Also, the chitosan has low levels of heavy metals, particularly in comparison to prior art chitosan produced from crustacea, and is typically less than 1.0 parts per million and preferably less than 0.5 parts per million. The improved color uniformity, lack of ash, and low heavy metals levels have significant advantages, depending upon the application. For example, for cosmetic purposes color uniformity and clarity of the chitosan can be very desirable. Similarly, the lack of ash results in improved clarity and purity, thus providing advantages for use in both medical and dietary applications. Low heavy metals levels also provide significant advantage when the chitosan is used for medical or dietary purposes.

Chitin-containing Biomass

The present invention is directed to chitosan recovered from microbial biomass, in particular fungal biomass, including yeast and filamentous fungi. Suitable microbial biomass may be obtained from *Aspergillus niger, Aspergillus terreus, Aspergillus oryzae, Candida guillermondii, Lactarius vellereus, Mucor rouxii, Penicillium chrysogenum, Penicillium notatum, Saccharomyces cerevisiae*; and in particular *Candida Guillermondii, Aspergillus niger,* or *Aspergillus terreus.* Although it is possible to generate biomass solely for the purpose of obtaining chitosan, the biomass most often is a by-product of other production processes. For example, citric-acid fermentation facilities use fungi to create citric acid. Traditionally, the fungal biomass from citric-acid fermentation has been discarded or used as fuel, feed, or fertilizer. However, the present invention allows extraction of high quality chitosan from this fungal biomass.

Biomass suitable for use in the present invention includes most types of chitin-containing microbial biomass, and in particular fungal biomass. The invention is particularly well suited to uses where the chitin levels exceed 5 percent of the dry biomass weight. Such biomass usually has between 5 and 25 percent chitin, and typically from 10 to 20 percent chitin, based upon dry weight of the biomass. In order to prepare the highest quality chitosan, it is sometimes desirable that the microbial biomass be produced in a substantially controlled manner having relatively uniform temperature and nutrient levels during the growth of the biomass.

Method of Obtaining Chitosan from Chitin-containing Fungal Biomass

The present invention is also directed, in part, to improved methods of producing chitosan from chitin-containing biomass. The chitosan produced by the improved methods shows desirable properties which make the chitosan well-suited for various applications. These properties include, in certain implementations, favorable levels of deacetylation, viscosity, color, and/or ash.

In general, the method comprises reacting chitin-containing biomass in a caustic solution followed by recovery of the chitosan from the solution. In one embodiment of the invention, the chitin-containing biomass is a fungal biomass reacted in a caustic solution of greater than 25 percent alkali at a reaction temperature from 105 to 125° C. for a reaction period of 10 to 16 hours to convert the chitin in the biomass to chitosan. More generally, the chitin-containing biomass is typically reacted in a caustic solution that is from 30 to 40 percent alkali. Suitable reaction temperatures for reacting the biomass are generally less than 125° C., and reaction periods are generally from 10 to 20 hours, and typically from 10 to 16 hours.

The method of obtaining chitosan from microbial biomass may also include washing the deacetylated biomass with a caustic solution; recovery of the chitosan; precipitating the chitosan, and drying the precipitated chitosan. A pre-treating step may also be used in which the microbial biomass is heated at with a caustic solution with a lower percent alkali prior to reacting it at a higher caustic solution. Typically the caustic concentration is initially below 10 percent and subsequently raised to greater than 25 percent during the pre-washing step.

Chitosan Uses

The improved chitosan can be advantageously used in various applications. These applications include pharmaceuticals, general medical uses, textiles and films, nutritional and dietary products, filtration products and methods, and various other industrial and consumer products and processes. Specific products and uses are briefly described below.

With regard to pharmaceuticals, the chitosan can be used in orally administrable pharmaceutical compositions, their derivatives, and salts thereof; in drug capsules; as a carrier for various pharmaceuticals, including anticancer agents; as a bone growth matrix and in various dental applications; and to reduce blood cholesterol levels.

The chitosan is also suitable for use in general medical applications, such as to make dressings made of cotton-like chitosan fibers, including non- woven, biodegradable wound and burn dressings; as a treatment for skin ulcerations; to make temporary artificial ligaments; to promote tissue regeneration; in swellable wound dressings; as encapsulating agents for cell transplantation; as a soft tissue, skin or bone growth matrix; and as wound-healing ointments, sutures, artificial ligaments, etc.

The chitosan is suitable for use in food and dietary products; including in beverages, in diet foods, and in health foods. The chitosan can be used as stabilizers, packaging films, preservative coatings, cholesterol and fat-reducing agents (including as a fat binding agent for dietary and non-dietary applications), and chewing gums. In addition, the chitosan can be used as a fining agent to clarify beverages; and to aid in the retention of post-cooked flavor in beef by binding to the iron in the beef and maintaining its flavor potential.

The chitosan can be used in various textile and film applications. These applications include use in anti-bacterial, mildew-proof and deodorant fibers for making underwear, socks, bed sheets for hospitals, bandages, diapers, pillow covers, gloves, towels, aprons, and bedding; and specialized cleaning absorbents, such as synthetic absorbent sponges. The chitosan can be incorporated into fabric for wrapping material for foods, tea bags, disposable warmers, etc.; and into antibacterial and freshness-preserving non-woven fabrics. In specific implementations the chitosan can be used as a coating on various fabrics, including rayon. The chitosan is suitable for use in water-permeable fabrics for sports and professional use, and methods for facilitating cloth production.

The improved chitosan can be incorporated and used in various cosmetic products. For example, the chitosan may be incorporated into hair shampoos, rinses, perming agents, colorants, sprays and tonics, skin creams and lotions, eye shadows, lipsticks, foundations, nail enamels, and other cosmetics, toothpastes and mouthwashes. The chitosan can be used in deodorant formulas to inhibit bacterial growth on the skin surface, thereby preventing perspiration odor. In hair styling products, chitosan adds desired form and strength, while preventing the hair from drying out or splitting. Also, the chitosan can be used in treatment of "orange peel skin" because of its ability to form a clear protective coating possessing moisture retention properties and being non-shellfish allergenic. In hair care products chitosan can form films with hair keratin. The chitosan can be used in pigments in color cosmetics; and can be used to coat dispersed pigment particles and soften the consistency of such pigmented cosmetics.

The chitosan has numerous uses in agriculture, including use in biodegradable films based on cellulose, starch and chitosan, may be decomposed by soil microbes, and can be used in agricultural and fisheries applications. Chitosan tends to increase root and stem growth and is can be effective in creating immunity to disease in plants. Furthermore, the chitosan can be used as a coating for delayed ripening of fruit, and as a seed treatment. The chitosan film has good wet and dry strength, and is suitable for agricultural applications such as tapes for seeds and spore bags for aver farming.

Various water treatment and filtration processes are amenable to use with the improved chitosan, such as use as micro porous or macro porous affinity filtration membranes for removal of metals, pesticides and PCBs. The chitosan can be used as for producing solid supports for various chromatographic methods, chelating agents, adsorbents, carries for enzymes or cells, and time-release bases for physiologically active substances; and can be used as treatments for organic (such as bioremediation) or heavy-metal pollutants and clarifiers for pools, spas, or natural bodies of water, as well as waste recovery. Specifically, chelating- based recovery systems for metals used in various industries, including electroplating, electronics manufacturing, metal finishing, photo processing and jewelry production may be used that contain chitosan. Chitosan adsorbents can be effective for removal of radio nuclides, removal of metals, pesticides and PCBs from liquids. In particular implementations the chitosan may be used as treatments for organic or heavy-metal pollutants and clarifiers for pools, spas, or natural bodies of water. Finally the chitosan can be used as a sewage treatment additive and chelating agent for removal of traces of heavy metals from aqueous solutions.

Numerous industrial applications are appropriate for use with the improved chitosan, including use in adhesives and as a coating to improve dyeing characteristics of glass fibers. Further, the improved chitosan can be used as a wet strength additive for paper, adhesives, photographic and printing applications, and can act as a 'retention aid' in paper. Specific paper applications include use as a retention agent in the manufacture of paper. As such, it acts to retain titanium dioxide, ash components, calcium carbonate, silica derivatives, and pulp fines. Chitosan can also be used as a printing aid to help within runability. The chitosan can help retain components such as ash (opacity, whitening agents) and fiber fines in the pulp mixture as it is being pressed into paper. The chitosan can also be used to improve the strength of a final paper product, which helps decrease potential down time during processing.

In addition, various other applications and uses for the chitosan are also appropriate.

Example Method of Obtaining Chitosan from Chitin-containing Biomass

The following example is provided to demonstrate recovery of chitosan from chitin in accordance with an implementation of the invention. In the example depicted, the chitosan was recovered under laboratory conditions. However, the invention is especially applicable to production of chitosan in large-scale manufacturing operations where particularly uniform sources of fungal biomass may be obtained.

250 grams of microbial biomass of *Aspergillus niger* was mixed with approximately 250 mL of a 4 percent by weight aqueous sodium hydroxide solution. The alkali biomass solution was heated in an autoclave for 30 minutes at a temperature of 120° C. in order to pre-treat the biomass and aid in the removal of proteins, lipids, and various colored impurities. After heating, the warm solution was filtered, and the solids washed with deionized water until the water ran substantially clear. This pre-treated biomass can be immediately processed to deacetylate the chitin, but can optionally be stored.

For this example, approximately 200 grams of pre-treated biomass, which often contains 80 to 86 percent water, was placed in a polypropylene bottle on a top load balance, followed by addition of 180 grams of 50 percent aqueous solution of sodium hydroxide, and 60 grams of sodium hydroxide pellets. The reaction mixture typically contains 32 to 38 percent sodium hydroxide, 55 to 65 percent water, and 3 to 9 percent dry pre-treated biomass.

A strongly exothermic reaction occurred, and the sodium hydroxide pellets dissolved into solution with the biomass and water. The polypropylene bottle containing the biomass in the alkali sodium hydroxide solution was placed in a preheated oven at approximately 120° C. The bottle was loosely covered in order to allow escape of gases.

The solution was maintained at a temperature of 120° C. for 16 hours, after which it was removed from the oven and 200 mL of near-boiling water was gently added to the solution. This hot mixture was filtered through filter cloth, and the solids rinsed with additional hot deionized water. The solids, containing a chitosan-glucan complex, were rinsed with approximately 500 mL of water approximately 10 times until the pH of the filtered solution was below 9.

After rinsing, the solids were transferred to a beaker and glacial acetic acid was added until a pH of between 3.5 and 5.0 was obtained. The mixture was stirred for approximately 10 minutes to extract chitosan from the glucan, and the mixture centrifuged. The supernatant was collected in an Erlenmeyer flask Optionally, the residue in the centrifuge container may be rinsed with a slightly acidic solution to remove any additional chitosan and re-centrifuged. The supernatant containing dissolved chitosan from the two centrifuge steps may then be combined and further processed.

The solution from the supernatant was moderately turbid, and was filtered through a 1.5 $\mu$m membrane filter followed by filtration through a 0.7 $\mu$m membrane filter. The filtration through the 0.7 $\mu$m filter was repeated until no visible suspension was observed in the solution. After filtration, a solution of 10 percent sodium hydroxide was added to the filtered chitosan-containing solution, until a pH of between 10.5 and 11.5 was obtained, at which time a white solid containing chitosan precipitated from the solution. The mixture was set aside for 10 minutes until the precipitate separated out of the solution. The mixture was decanted, followed by rinsing with water to remove excess sodium hydroxide. The basic mixture was placed in a centrifuge bottle, which was centrifuged and decanted. Additional deionized water was added to the centrifuge residue, which was shaken to suspend all solids, centrifuged again, and decanted. These steps of centrifuging, decanting, and washing were repeated until the pH dropped below 9.0. Care was taken to reduce the time that the chitosan at excessively high or low pH for long periods of time to avoid depolymerization or degradation. The resulting residue was freeze dried.

| The recovered chitosan had the following characteristics: | |
|---|---|
| viscosity (centipoise) | 1 to 10 |
| turbidity | 5 to 20 NTU |
| ash percent | 0.20 to 0.40 |
| color | 120 to 170 APHA |
| deacetylation | 92 to 97 percent |

Viscosity was measured using a Brookfield DV-II viscometer, which measures fluid resistance using a moving pendulum in motion. A solution of 1 percent chitosan and 1 percent acetic acid in water was prepared and mixed until all chitosan was in solution. The viscometer controls were set for a large spindle and a temperature of 25° C., after which a 16 ml sample was placed within the sample tube. This sample tube was positioned in the mounting channel of the viscometer, and the viscosity measured after approximately 5 seconds.

Turbidity was measured using a HACK Ratio/XR turbidometer on a sample of 1 percent by weight chitosan (based on dry weight) in 1 percent by weight aqueous acetic acid.

The ash content was measured using a muffle furnace and hot plate. The muffle furnace was heated to 550° C. (within a range of 25 degrees), and a sample of chitosan was added to a crucible of a known weight. This sample and crucible were heated in the muffle furnace for 10 hours until washing was complete, after which the crucible was placed in a desiccator to cool for 60 minutes. After this cooling period, the weight of the crucible was measured, and the percent ash calculated using the following formula:

% Ash=((Final Crucible Weight)−(Initial Crucible Weight))/ (Sample Weight)×100

Color was measured using an Aquatester by Orbeco-Hellige on a sample of 1 percent by weight chitosan (based on dry weight) in 1 percent by weight aqueous acetic acid.

Deacetylation was measured using nuclear magnetic resonance (NMR) spectroscopy. Pre-samples were prepared over a period of about 2 to 3 hours. To prepare the pre-samples, approximately 50 milligrams of chitosan-containing material was mixed in de-ionized water (5 mL) in a 10 mL test tube. Approximately 1 to 2 drops of formic acid were added to the sample to dissolve solids, after which the test tube was vigorously shaken to dissolve the chitosan. After the chitosan was dissolved, approximately 10 percent sodium hydroxide was added to precipitate the chitosan. The solid was centrifuged and the supernatant decanted. Approximately 1 ml of deionized water was added to the residue. The tube was vigorously shaken to mix the solid residue into the solution, and the solution was centrifuged. The shaking and centrifuging steps were repeated until the supernatant pH was near neutral, at which point 5 mL of water was added to the collected solid, and small amounts of formic acid were added to completely dissolve the solid. These steps were repeated. The obtained solution was frozen and freeze-dried.

Samples were prepared by measuring approximately 15 to 20 milligrams of dried sample into a small vial. About 1.5 milliliters of deuterium hydroxide ($D_2O$) was added to the sample, which was shaken vigorously to dissolve completely, and the NMR spectrum analyzed and used to determine the degree of deacetylation.

The above specification, examples and data provide a description of the compositions and methods of the invention. Since many embodiments of the invention can be made without departing from the spirit and scope of the invention, the invention resides in the following claims.

We claim:

1. A chitosan containing material derived from fungal biomass, the chitosan containing material having:
   greater than 85 percent deacetylation of N-acetyl groups in the chitin and not including material from phyto-plankton, crustaceans, or molluscs, wherein a 1% solution of the chitosan containing material has a turbidity of less than 20 NTUs.

2. The chitosan containing material derived from fungal biomass of claim 1, wherein a 1 percent by weight solution of the chitosan containing material in 1 percent aqueous acetic acid has a viscosity of less than 25 centipoise at 25° C.

3. The chitosan containing material derived from fungal biomass of claim 1, wherein a 1 percent by weight solution of the chitosan containing material in 1 percent aqueous acetic acid has a viscosity of less than 15 centipoise at 25° C.

4. The chitosan containing material of claim 1, wherein the chitosan containing material has greater than 90 percent deacetylation of the N-acetyl groups in the chitin.

5. The chitosan containing material of claim 1, wherein the chitosan containing material has greater than 93 percent deacetylation of the N-acetyl groups in the chitin.

6. The chitosan containing material of claim 1, wherein the chitosan containing material has greater than 95 percent deacetylation of the N-acetyl groups in the chitin.

7. The chitosan containing material of claim 1, wherein the chitosan containing material has ash levels below 0.50 percent.

8. The chitosan containing material of claim 1, wherein a 1 percent by weight solution of the chitosan containing material in 1 percent aqueous acetic acid has a turbidity of between 5 and 20 NTU.

9. The chitosan containing material of claim 1, wherein the chitosan is derived from substantially uniform microbial fungal sources.

10. The chitosan containing material of claim 1, wherein less than 15 percent of the amine groups are acetylated and said material is obtained from microbial biomass.

11. A chitosan containing material derived from fungal biomass, the chitosan containing material having greater than 85 percent deacetylation of N-acetyl groups in the chitin and not including material from phyto-plankton, crustaceans, or mollusks, wherein the chitosan is derived from *Candida Guillermondii, Aspergillus niger, Aspergillus terreus,* and combinations thereof, wherein a 1% solution of the chitosan containing material has a turbidity of less than 20 NTUs.

12. The chitosan containing material derived from fungal biomass of claim 11, wherein a 1 percent by weight solution of the chitosan containing material in 1 percent aqueous acetic acid has a viscosity of less than 25 centipoise at 25° C.

13. The chitosan containing material derived from fungal biomass of claim 11, wherein a 1 percent by weight solution of the chitosan containing material in 1 percent aqueous acetic acid has a viscosity of less than 15 centipoise at 25° C.

14. The chitosan containing material of claim 11, wherein the chitosan containing material has greater than 90 percent deacetylation of the N-acetyl groups in the chitin.

15. The chitosan containing material of claim 11, wherein the chitosan containing material has greater than 93 percent deacetylation of the N-acetyl groups in the chitin.

16. The chitosan containing material of claim 11, wherein the chitosan containing material has greater than 95 percent deacetylation of the N-acetyl groups in the chitin.

17. The chitosan containing material of claim 11, wherein the chitosan containing material has ash levels below 0.50 percent.

18. The chitosan containing material of claim 11, wherein a 1 percent by weight solution of the chitosan containing material in 1 percent aqueous acetic acid has a turbidity of between 5 and 20 NTU.

19. The chitosan containing material of claim 11, wherein the chitosan is derived from substantially uniform microbial fungal sources.

20. The chitosan containing material of claim 11, wherein less than 15 percent of the amine groups are acetylated and said material is obtained from microbial biomass.

* * * * *